United States Patent [19]

Adachi et al.

[11] 4,266,013
[45] May 5, 1981

[54] DIRECT POSITIVE SILVER HALIDE LIGHT-SENSITIVE MATERIAL AND METHOD OF FORMING DIRECT POSITIVE IMAGE

[75] Inventors: Keiichi Adachi; Shigeo Hirano; Nobuyuki Tsujino, all of Minami-ashigara, Japan

[73] Assignee: Fuji Photo Film Co., Ltd., Ashigara, Japan

[21] Appl. No.: 961,827

[22] Filed: Nov. 17, 1978

[30] Foreign Application Priority Data

Nov. 28, 1977 [JP] Japan ................................ 52/142469

[51] Int. Cl.$^3$ ................................................ G03C 1/36
[52] U.S. Cl. ................................. 430/410; 430/379; 430/505; 430/559; 430/570; 430/580; 430/581; 430/592; 430/591; 430/598; 564/27
[58] Field of Search ................ 96/76 R, 77, 95, 99, 96/64, 129, 130, 139, 140; 260/552 R; 430/410, 379, 505, 559, 570, 580, 581, 592, 591, 598

[56] References Cited

U.S. PATENT DOCUMENTS

| | | |
|---|---|---|
| 3,227,552 | 1/1966 | Whitmore ................................. 96/3 |
| 4,030,925 | 6/1977 | Leone et al. ............................ 96/95 |
| 4,080,207 | 3/1978 | Leone et al. ............................ 96/95 |

Primary Examiner—Won H. Louie, Jr.
Attorney, Agent, or Firm—Sughrue, Rothwell, Mion, Zinn and Macpeak

[57] ABSTRACT

A light-sensitive silver halide photographic material comprising a support having thereon a layer containing a compound represented by the formula (I):

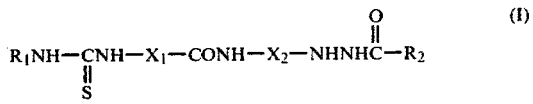

wherein $R_1$ represents an aliphatic or aromatic residue; $R_2$ represents a hydrogen atom, an aliphatic or an aromatic residue; and $X_1$ and $X_2$, which may be the same or different, each represents a divalent aromatic group; and a method of forming a direct positive image which comprises processing a light-sensitive silver halide photographic material having a support carrying thereon an internal latent image type silver halide emulsion layer in the presence of the compound represented by the said formula (I). The compound is particularly effective in combination with diffusible dye releasing (DRR) compounds having o-hydroxyarylsulfamoyl groups.

16 Claims, No Drawings

DIRECT POSITIVE SILVER HALIDE LIGHT-SENSITIVE MATERIAL AND METHOD OF FORMING DIRECT POSITIVE IMAGE

BACKGROUND OF THE INVENTION

1. Field of the Invention

The present invention relates to a method of forming a direct positive image and a silver halide photographic light-sensitive material by which direct positive photographic images are formed, and more particularly, to a photographic light-sensitive material, whose photographic emulsion layers or other hydrophilic colloid layers contain a novel compound as a fogging agent.

2. Description of the Prior Art

In the field of silver halide photography, a technique in which positive photographic images are obtained without going through negative images or intermediate processing producing negative images is called direct positive photography, and photographic light-sensitive materials and photographic emulsions using such a photographic technique are called direct positive light-sensitive materials and direct positive photographic emulsions, respectively.

A variety of direct positive photographic techniques are known. The most useful methods are methods in which silver halide grains which have previously been fogged are exposed to light in the presence of a desensitizer followed by development, and methods comprising exposing silver halide emulsion containing silver halide grains having light-sensitive specks mainly inside the silver halide grains to light and then developing the exposed emulsion in the presence of a fogging agent. The present invention relates to the latter technique. Silver halide emulsions possessing light-sensitive specks in the inside of the silver halide grains and forming latent images mainly inside the grains are referred to as an internal latent image type silver halide emulsions and thus distinguished from silver halide grains which form latent images mainly on the surface of the grains and referred to as surface latent image type silver halide grains.

A method for obtaining direct positive images by surface-developing an internal latent image type silver halide photographic emulsion in the presence of a fogging agent, and photographic emulsions employed for such a method are disclosed in U.S. Pat. Nos. 2,456,953, 2,497,875, 2,497,876, 2,588,982, 2,592,250, 2,675,318 and 3,227,552. British Pat. Nos. 1,011,062 and 1,151,363, Japanese Pat. No. 29405/1968, etc.

In the internal latent image type method for obtaining direct positive images, the fogging agent can be incorporated into a developing solution, however, by incorporating the fogging agent into photographic emulsion layers or associated layers of the light-sensitive material and thereby adsorbing it onto the surface of the silver halide grains, better reversal characteristics can be obtained.

As fogging agents which are employed in the above-described methods for obtaining direct positive images, there are hydrazine and derivatives thereof as described in U.S. Pat. Nos. 2,563,785, 2,588,982 and 3,227,552, respectively. In particular, U.S. Pat. No. 3,227,552 discloses that hydrazide and hydrazine type compounds which are derivatives of hydrazine can be incorporated not only in developing solution but also in light-sensitive layers.

However, when hydrazine compounds are incorporated into the emulsion layer, the compounds must be employed in a considerably high concentration (e.g., about 2 g per 1 mol of silver), and in addition, because the fogging agent is transferred from the emulsion layer to the developing solution during development processing the concentration of the fogging agent in emulsion varies and unevenness in the maximum density results (at the non-exposed areas), i.e., the fogging effect becomes non-uniform, in the case of multilayer color light-sensitive material, among the emulsion layers.

Furthermore, it is known that these fogging agents evolve nitrogen gas during fogging. This gas gathers in a film to form gas bubbles, which sometimes imparts unexpected damage to photographic images.

In order to avoid these shortcomings, fogging agents comprising a heterocyclic quaternary salt compounds described in U.S. Pat. Nos. 3,615,615, 3,719,494, 3,734,738 and 3,759,901, Japanese patent application (OPI) Nos. 3426/1977 and 69613/1977 (The term "OPI" as used herein refers to a "published unexamined Japanese patent application") have been used.

However, in most cases, sensitizing dyes are incorporated into the silver halide emulsion for spectral sensitization, and particularly in color light-sensitive materials, layers which are respectively sensitive to both green light and red light in addition to a layer sensitive to blue light are essentially required and emulsions in the green sensitive layer and red sensitive layer necessarily contain sensitizing dyes. In direct positive emulsions, where fogging agents are contained together with sensitizing dyes sensitive to green light and red light, competitive adsorption in the silver halide emulsion occurs between the sensitizing dyes and the quaternary salt fogging agent. If a fogging agent in an amount sufficient to form the fogging centers is incorporated into the emulsion, spectral sensitization is prevented. On the other hand, if a spectrally sensitizing dye in a concentration sufficient to obtain desired spectral sensitization is incorporated into the emulsion, the formation of the fogging center is prevented.

One means for overcoming this disadvantage, wherein a sensitizing dye having a nucleating substituent in the dye molecule is employed, is disclosed in U.S. Pat. No. 3,718,470.

However, when nucleating activity as well as spectrally sensitizing activity are simultaneously imparted to one molecule, the use of the dye in an appropriate amount for the spectral sensitization is insufficient for the nucleating activity, and on the other hand, the use of the dye in an amount sufficient for the nucleating activity is inappropriate for the spectral sensitization.

In addition, a disadvantage which is common to the hydrazine type compounds and heterocyclic quaternary salt compounds is their large temperature-dependency for the nucleating activity. That is, if the developing temperature is low, the lower is the nucleating activity, and if the developing temperature is high, the sensitivity is reduced.

In order to eliminate this disadvantage, it has been proposed in U.S. Pat. No. 4,030,925 (corresponding to German patent application (OLS) No. 2,635,316) and U.S. Pat. No. 4,031,127 (corresponding to German patent application (OLS) No. 2,635,317) that acyl hydrazinophenylthiourea compound be employed.

However, in this field of art, it has long been desired to develop more improved fogging agents having less temperature-dependency (upon processing) with direct positive system not only using the p-hydroxyarylsulfonamide type dye image-providing materials as described in the aforementioned U.S. patents but also using dye image-providing materials different therefrom.

SUMMARY OF THE INVENTION

Accordingly, a first object of the present invention is to provide a method of forming a direct positive image and a direct positive light-sensitive material capable of obtaining uniform maximum density.

A second object of the present invention is to provide a direct positive photographic light-sensitive material containing a fogging agent (nucleating agent) which imparts a desired fogging (nucleating) activity without detracting from spectral sensitization.

A third object of the present invention is to provide a direct positive photographic light-sensitive material in which adequate spectral sensitization is provided and direct positive images having uniform and high maximum density are produced.

A fourth object of the present invention is to provide a direct positive photographic light-sensitive material which does not contaminate the developing solution.

A fifth object of the present invention is to provide a method of forming a direct positive image and a direct positive photographic light-sensitive material having less dependency upon the developing temperature.

A sixth object of the present invention is to provide a color diffusion transfer photographic light-sensitive material which has the aforementioned various properties.

DETAILED DESCRIPTION OF THE INVENTION

The aforementioned objects of the present invention are achieved by incorporating a fogging agent represented by the formula (I) set forth below into at least one hydrophilic colloid layer in a silver halide light-sensitive material or into a processing solution such as a surface developing solution and a "pre-bath" used prior to the developing step, preferably an internal latent image type silver halide photographic emulsion layer or an adjacent hydrophilic colloid layer.

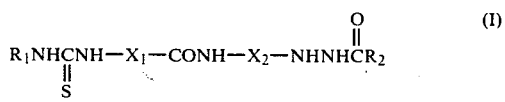
(I)

wherein $R_1$ represents an aliphatic or an aromatic residue; $R_2$ represents a hydrogen atom, an aliphatic or an aromatic residue; and $X_1$ and $X_2$, which may be the same or different, each represents a divalent aromatic residue.

In more detail, the aliphatic residue for $R_1$ and $R_2$ includes a substituted or unsubstituted straight chain, branched chain or cyclo alkyl group and a substituted or unsubstituted alkenyl group. The straight chain and branched chain alkyl group for $R_1$ is an alkyl group having 1 to 10 carbon atoms and preferably 1 to 8 carbon atoms. Specific examples thereof include a methyl group, an ethyl group, an isobutyl group, a t-octyl group, etc. The alkyl group for $R_2$ comprises, for example, 1 to 6 carbon atoms, e.g., a methyl group, an ethyl group, a propyl group, etc.

Further, the cycloalkyl group for $R_1$ and $R_2$ comprises, for example, 1 to 6 carbon atoms; specific examples thereof including a cyclopropyl group, a cyclohexyl group, an adamantyl group, etc.

The alkenyl group has preferably 3 to 20 carbon atoms and includes, e.g., an alkyl group and a crotonyl group.

Examples of the substituents for the alkyl or alkenyl group of $R_1$ and $R_2$ include an alkoxy group preferably having 1 to 20 carbon atoms (e.g., a methoxy group, an ethoxy group, a propoxy group and a butoxy group), a halogen atom (e.g., chlorine, bromine, fluorine and iodine), an aryl group including a monocyclic aryl group and a bicyclic aryl groups and preferably having 6 to 20 carbon atoms (e.g., a phenyl group, a p-chlorophenyl group and a p-methylphenyl group), a hydroxy group, an alkoxycarbonyl group preferably having 2 to 13 carbon atoms, an aryloxycarbonyl group preferably having 7 to 11 carbon atoms, an amido group preferably having 2 to 13 carbon atoms, and an acyloxy group having 2 to 13 carbon atoms. Specific examples of the substituted alkyl groups for $R_1$ and $R_2$ are, for example, a 3-methoxypropyl group, a 4-chlorocyclohexyl group, a benzyl group, a p-methylbenzyl group and a p-chlorobenzyl group.

On the other hand, the aromatic residues for $R_1$ and $R_2$ include a monocyclic aryl group and a bicyclic aryl group, i.e., a substituted or unsubstituted phenyl group and a substituted or unsubstituted naphthyl group. Examples of the substituents for these substituted aryl groups include an alkyl group preferably having 1 to 18 carbon atoms and, in addition, those substituents as set forth above with regard to alkyl groups for $R_1$ and $R_2$. Specific examples of the substituted aryl group for $R_1$ and $R_2$ include, e.g., a p-methoxyphenyl group, a tollyl group, a p-chlorophenyl group and an m-fluorophenyl group.

The divalent aromatic residues for $X_1$ and $X_2$ include a substituted or unsubstituted phenyl group and a substituted or unsubstituted naphthyl group. Examples of the substituents for these substituted arylene groups for $X_1$ and $X_2$ are those groups as described above relative to substituted aryl groups for $R_1$ and $R_2$. It is not preferred that the substituent for the substituted arylene groups for $X_2$ be an electron-accepting group. Of the $X_1$ and $X_2$ groups defined above, a phenylene group is the most preferred. In other words, the connecting group formed between the

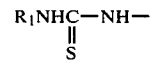

group and the

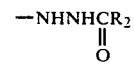

group is preferably

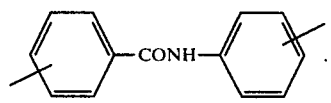

More specifically, the

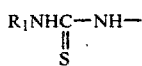

group is connected to the

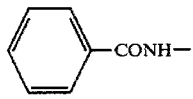

group at the meta or para position, and the

group is connected with the

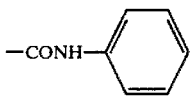

group at the meta or para position thereof.

When the fogging agent of the present invention is employed, the following various effects are obtained.

(1) The temperature-dependency of processing is less.

(2) No deterioration of images due to evolution of nitrogen gas is encountered.

(3) The amount of the fogging agent employed is reduced.

(4) Adsorbing capability of silver halide is strong so that fogging activity effectively occurs. (The amount of fogging agent employed may be reduced and, thus, spectral sensitization is not damaged.)

(5) Visible light is not absorbed such that no desensitization is caused.

Specific examples of the fogging agents which are effective in the present invention are illustrated below.

Compound 1

1-Formyl-2-{4-[3-(3-phenylthioureido)benzamido]phenyl}hydrazide

Compound 2

1-Acetyl-2-{4-[4-(3-phenylthioureido)benzamido]phenyl}hydrazide

Compound 3

1-Acetyl-2-{4-[3-(3-phenylthioureido)benzamido]phenyl}hydrazide

Compound 4

1-Formyl-2-{4-[4-(3-phenylthioureido)benzamido]phenyl}hydrazide

Compound 5

1-Acetyl-2-{4-[4-(3-allylthioureido)benzamido]phenyl}hydrazide

Compound 6

2-{4-[4-(3-ethylthioureido)benzamido]phenyl}-1-hydrazide

Compound 7

1Formyl-2-{3-[3-(3-phenylthioureido)benzamido]phenyl}hydrazide

Compound 8

1-Formyl-2-{3-[4-(3-phenylthioureido)benzamido]phenyl}hydrazide

Compound 9

2-{4-[3-(3-allylthioureido)benzamido]phenyl}-1-formylhydrazide

Compound 10

2-{4-[3-(3-(4-chlorophenyl)thioureido)benzamido]phenyl}-1-formylhydrazide

Compound 11

1-Acetyl-2-{4-[4-(3-n-butylthioureido)benzamido]phenyl}hydrazide

Compound 12

1-Acetyl-2-{4-[4-(3-cyclohexylthioureido)benzamido]phenyl}hydrazide

Compound 13

1-Acetyl-2-{3-[4-(3-phenylthioureido)benzamido]phenyl}hydrazide

Compound 14

1-Benzoyl-2-{4-[3-(3-ethylthioureido)benzamido]phenyl}hydrazide

Compound 15

1-(4-chlorobenzoyl)-2-{3-[3-(3-phenylthioureido)benzamido]phenyl}hydrazide

Compound 16

1-Acetyl-2-{3-[4-(3-methylthioureido)benzamido]phenyl}hydrazide

Compound 17

2-{4-[3-(3-ethylthioureido)benzamido]phenyl}-1-formylhydrazide

Compound 18

1-Formyl-2-{4-[3-(3-t-octylthioureido)benzamido]phenyl}hydrazide

Compound 19

2-{4-[3-(3-cyclohexylthioureido)benzamido]phenyl}-1-formylhydrazide

Compound 20

1-Acetyl-2-{4-[3-(3-allylthioureido)benzamido]phenyl}hydrazide

Compound 21

1-Acetyl-2-{3-[3-(3-phenylthioureido)benzamido]phenyl}hydrazide

Compound 22

2-{4-[3-(3-phenylthioureido)benzamido]phenyl}-1-propionylhydrazide

Compound 23

1-Acetyl-2-{4-[3-(3-ethylthioureido)benzamido]phenyl}hydrazide

Compound 24

2-{3-[4-(3-allylthioureido)benzamido]phenyl}-1-formylhydrazide

Compound 25

1-Formyl-2-{4-[3-(3-(4-methoxyphenyl)thioureido)-benzamido]phenyl}hydrazide

Compound 26

2-{4-[3-(3-allylthioureido)benzamido]phenyl}-1-(3-methylbenzoyl)hydrazide

Compound 27

1-Acetyl-2-{4-[3-(3-(3-fluorophenyl)thioureido)benzamido]phenyl}hydrazide

Compound 28

1-Acetyl-2-{4-[3-(3-(4-methoxyphenyl)thioureido)-benzamido]phenyl}hydrazide

Compound 29

2-{4-[4-(3-isobutylthioureido)benzamido]phenyl}-1-formylhydrazide

Compound 30

1-Formyl-2-{4-[4-(3-(4-methoxyphenyl)thioureido)-benzamido]phenyl}hydrazide

A general synthetic method for forming the fogging agent employed in the present invention is as follows:
Step 1:

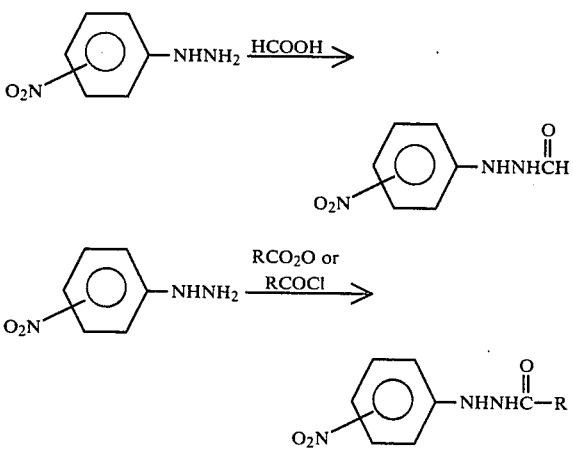

By reacting 1 mol of 4- or 3-nitrophenylhydrazine with about 2 to about 5 mols, preferably 2 to 3 mols, of formic acid in the absence of a solvent or in the presence of about 0.5 to about 3 l, preferably 1 to 1.5 l, of a solvent such as acetonitrile, ethanol, methyl Cellosolve, etc., for about 1 to about 5 hours, preferably 2 to 3 hours, with heating at about 50° to about 100° C., preferably 60° to 70° C., and agitating, 1-formyl-2-(4- or 3-nitrophenyl)hydrazide can be obtained. Corresponding 1-acyl-2-(4- or 3-nitrophenyl)hydrazides can be prepared by reacting 1 mol of 4- or 3-nitrophenylhydrazine with about 1 to about 1.5 mol, preferably 1 to 1.1 mol, of an acid anhydride (RCO₂O) or acid halide (RCOCl) in about 0.5 to about 3 of a solvent such as acetonitrile, tetrahydrofuran, dimethylacetamide, etc., in the presence of about 1 to about 3 mols, preferably 1 to 1.5 mols, of a deoxidizing agent such as triethylamine, pyridine, etc., at about 0° to about 50° C., preferably 5° to 20° C., for about 1 to about 5 hours, preferably 2 to 3 hours. (Cf. "Review on Acylation of Amine by

Sonntag *Chem. Rev.*, 52, pp. 258–294 (1953).)
Step 2:

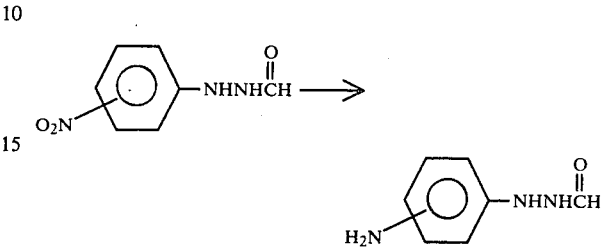

By catalytically reducing with hydrogen gas 1 mol of nitrophenylhydrazide derivatives in about 0.5 to about 3 l, preferably 1 to 2 l, of a solvent such as alcohols, e.g., ethanol, methyl Cellosolve, etc., and dioxane, in the presence of about 1 to about 20 g, preferably 2 to 5 g, of palladium on carbon as a catalyst at room temperature (about 10° to 25° C.) to about 100° C., preferably 20° to 30° C., at a hydrogen gas pressure of about 1 to about 120 kg/cm², preferably 20 to 50 kg/cm², for about 1 to about 10 hours, preferably 2 to 3 hours, corresponding 4- or 3-aminophenylhydrazide derivatives can be obtained. (Cf. R. L. Augustine: "Catalytic Hydrogenation", pp. 36 & 152, Marcel Dekker, New York (1965).) These 4- or 3-aminophenylhydrazide derivatives can also be obtained with ease by heating 1 mol of 4- or 3-nitrophenylhydrazide derivatives together with about 50 to about 500 g, preferably 100 to 200 g, of reduced iron in a mixture of about 0.5 l to about 5 l of a solvent such as alcohols, e.g., ethanol, isopropyl alcohol, etc., or dioxane and about 0.05 to about 0.5 l, preferably 0.1 to 0.2 l, of water in the presence of about 5 to about 50 g, preferably 10 to 20 g, of a catalyst such as ammonium chloride, iron chloride, ammonium sulfate, barium chloride, calcium chloride, etc., with ammonium chloride being preferred at about 50° to about 120° C., preferably 80° to 100° C., for about 1 to about 5 hours, preferably 2 to 3 hours (cf. Yoshiro Ogata: "Oxidation and Reduction of Organic Compounds", pp. 644–650, Nankodo, Tokyo (1963)).

Step 3:

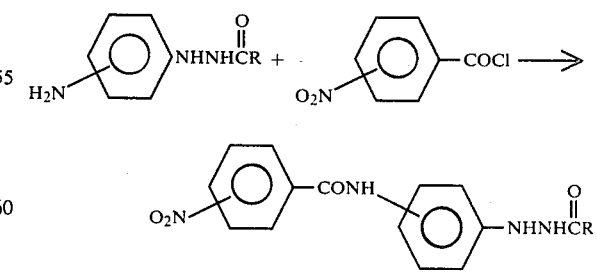

4- or 3-Aminophenylhydrazide can be converted into corresponding nitrobenzamidophenylhydrazide derivatives by reacting 1 mol of it with 4- or 3-nitrobenzoyl chloride in about 0.5 to about 3 l, preferably 1 to 1.5 l, of a solvent such as acetonitrile, tetrahydrofuran, dimethylacetamide, etc., in the presence of about 1 to about 3 mols, preferably 1 to 1.5 mols, of a deoxidizing agent such as trimethylamine, pyridine, etc., at about 0° to about 100° C., preferably 5° to 50° C., for about 1 to about 5 hours, preferably 2 to 3 hours (cf. "Review of Acylation of Amine by

Sonntag *Chem. Rev.*, 52, pp. 258–294 (1953)).
Step 4:

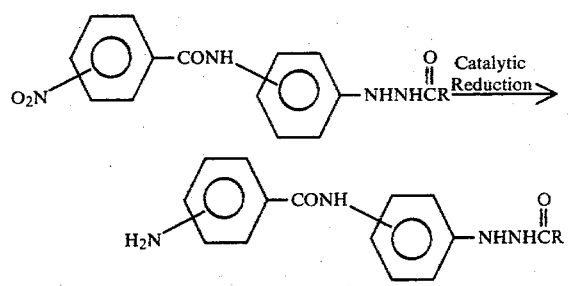

This catalytic reduction can be carried out in the same manner as in Step 2 above.
Step 5:

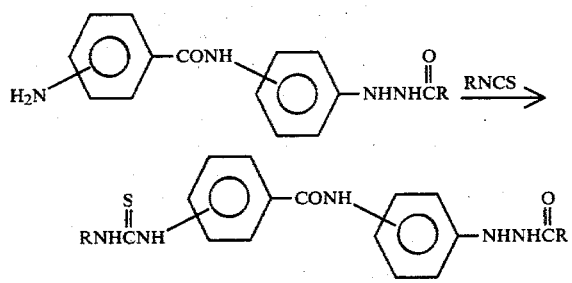

By reacting 1 mol of the aminobenzamidophenylhydrazide compound with an arylisothiocyanate such as phenylisothiocyanate, etc., an alkylisothiocyanate such as ethylisothiocyanate, etc., or an alkenylisothiocyanate such as allylisothiocyanate, etc., in about 1 to about 50 l, preferably 2 to 20 l, of a solvent such as an alcohol, e.g., methanol, ethanol, isopropyl alcohol, methyl Cellosolve, etc., dioxane, tetrahydrofuran, dimethylformamide, dimethylacetamide, dimethylsulfoxide, etc., at about 20° to about 100° C., preferably 40° to 60° C., for about 1 to about 8 hours, preferably 2 to 3 hours, the object compounds can be obtained (cf. E. Müller: "Methoden der Organischen Chemie", Band IX, Schwefel-Selen-Tellur-Verbindungen, Georg Thieme Verlag, Stuttgart, (1955), pp. 889–894).

Specific synthesis examples are illustrated below.

SYNTHESIS OF STARTING MATERIALS

Preparation 1:
1-Formyl-2-(4-nitrophenyl)hydrazide

To 1.6 l of acetonitrile was added 459 g of 4-Nitrophenylhydrazine. Then, 322 g of formic acid was slowly added to the mixture to produce a homogeneous solution. Crystals precipitated 20 minutes later. After the reaction continued for further 2 hours at 80° C. of inner temperature (i.e., the temperature of the internal portion of the container used for a reaction), the system was cooled. The crystals were removed by filtration and washed with acetonitrile. After drying, 493 g of 1-Formyl-2-(4-nitrophenyl)hydrazide was obtained; m.p.: 184°–186° C.

Preparation 2:
1-Formyl-2-(4-aminophenyl)hydrazide

In 1,600 ml of ethanol, 30 g of 1-formyl-2-(4-nitrophenyl)hydrazide was catalytically reduced at room temperature in the presence of a palladium-carbon catalyst. The reaction liquid was filtered and the filtrate was evaporated to dryness to obtain 20.5 g of white solid 1-Formyl-2-(4-aminophenyl)hydrazide; m.p.: 123°–125° C.

Preparation 3:
1-Formyl-2-(3-nitrophenyl)hydrazide

3-Nitrophenylhydrazide instead of 4-Nitrophenylhydrazide was reacted in a manner similar to Preparation (1) above to obtain 430 g of 1-Formyl-2-(3-nitrophenyl)hydrazide; m.p.: 168°–169° C.

Preparation 4:
1-Formyl-2-(3-aminophenyl)hydrazide

1-Formyl-2-(3-nitrophenyl)hydrazide was reacted in a manner similar to Preparation (2) above to obtain 21.0 g of 1-Formyl-2-(3-aminophenyl)hydrazide; m.p.: 108°–113° C.

Preparation 5:
1-Benzoyl-2-(4-nitrophenyl)hydrazide

In 200 ml of benzene was dissolved 30 g of 4-Nitrophenylhydrazine and 45 g of benzoic acid. The solution was heated under reflux for 3 hours. The reaction solution was poured into ice water. The resulting product was taken out by filtration, washed with ethanol and dried to obtain 40 g of 1-Benzoyl-2-(4-nitrophenyl)hydrazide; m.p.: 194°–196° C.

Preparation 6:
1-Benzoyl-2-(4-aminophenyl)hydrazide

1-Benzoyl-2-(4-nitrophenyl)hydrazide was catalytically reduced in a manner similar to Preparation (2) above to obtain 22 g of 1-Benzoyl-2-(4-aminophenyl)hydrazide; m.p.: 135°–137° C.

Preparation 7:
1-Formyl-2-[4-(3-nitrobenzamido)phenyl]hydrazide

In 500 ml of acetonitrile were dissolved 68.2 g of 1-Formyl-2-(4-aminophenyl)hydrazide and 60 ml of triethylamine. To the solution was added dropwise 70 g of 3-nitrobenzoyl chloride with stirring while keeping the inner temperature below 50° C. to precipitate crystals. After heating was continued for an additional 2 hours at 60° C., the reaction mixture was cooled and then poured into water. The resulting crystals were removed by filtration. Upon recrystallization from ethanol, 72.8 g of 1-Formyl-2-[4-(3-nitrobenzamido)phenyl]hydrazide was obtained; m.p.: 185°–187° C.

Preparation 8:
1-Acetyl-2-[4-(4-nitrobenzamido)phenyl]hydrazide

4-Nitrobenzoyl chloride was reacted with 1-acetyl-2-(4-aminophenyl)hydrazide obtained in a manner similar to Preparation (1) or (2) above in a manner similar to Preparation (7) above to obtain 78.3 g of 1-Acetyl-2-[4-(4-nitrobenzamido)phenyl]hydrazide; m.p.: 257°–260° C.

SYNTHESIS EXAMPLE 1

Synthesis of Compound 1

A mixture of 800 ml of isopropanol, 80 ml of water, a small amount of ammonium chloride (approximately 8 g) and 12 g of 1-formyl-2-[4-(3-nitrobenzamido)phenyl]-hydrazide was heated on a steam bath while stirring. To the mixture was added 80 g of iron powder. The mixture was refluxed for 1 hour. The reaction liquid was filtered. To the filtrate was added 11 g of phenyl isothiocyanate. The mixture was kept at 50° C. for 3 hours. The reaction liquid was then poured into an equal amount of water. The precipitated crystals were removed by filtration. Upon recrystallization from acetonitrile, 8.4 g of Compound 1 was obtained; m.p.: 186°–187° C.

SYNTHESIS EXAMPLE 2

Synthesis of Compound 2

A mixture of 500 ml of methyl Cellosolve, 50 ml of water, a small amount of ammonium chloride and 15.7 g of 1-acetyl-2-[4-(4-nitrobenzamido)phenyl]hydrazide was heated on a steam bath with stirring. To the mixture was added 50 g of iron powder. The mixture was heated for 1 hour at inner temperature of 80° C. The reaction liquid was filtered. To the filtrate was added 27 g of phenyl isothiocyanate. The mixture was kept at 40°–50° C. for 1 hour to precipitate crystals. The system was cooled to room temperature and the crystals were removed by filtration. Upon recrystallization from a solvent mixture of 360 ml of dimethylformamide and 720 ml of isopropanol, 18 g of the Compound 2 was obtained; m.p.: 257°–260° C.

SYNTHESIS EXAMPLE 3

Synthesis of Compound 8

To 18 g of 1-formyl-2-[3-(4-nitrobenzamido)phenyl]-hydrazide (which had been prepared in a manner similar to Preparation (7)) were added 300 ml of isopropanol, 60 ml of water and a small amount of ammonium chloride. The mixture was then heated under reflux. Thereafter, 30 g of iron powder was added thereto. The mixture was heated under reflux for 40 minutes. The reaction liquid was filtered. To the filtrate was added 13.5 g of phenyl isothiocyanate. The mixture was reacted at 50°–60° C. for 2 hours. The precipitated crystals were removed by filtration. Upon recrystallization from a solvent mixture of 80 ml of dimethylformamide and 80 ml of water, 19 g of Compound 8 was obtained; m.p.: 181°–182° C.

SYNTHESIS EXAMPLE 4

Synthesis of Compound 5

Procedures similar to Synthesis Example 2 were repeated using allyl isothiocyanate in lieu of phenyl isothiocyanate to obtain 15 g of 1-acetyl-2-{4-[4-(3-allylthioureido)benzamido]phenyl}hydrazide; m.p.: 218°–232° C. (decomposed).

The other compounds can be synthesized in a manner similar to above compound.

In the direct positive light-sensitive material of the present invention, it is preferred that the compound represented by the formula (I) be incorporated into the internal latent image type silver halide emulsion, however, the compound can also be incorporated into a contiguous hydrophilic colloid layer. Such a layer can be any layer of an intermediate layer, a filter layer, an antihalation layer, etc., having any function, as long as the fogging agent is not prevented from diffusing into the internal latent image type silver halide emulsion.

It is desired that the fogging agent of the present invention in layers be present in an amount that gives a suitable maximum density (for example, above 2.0) when the internal latent image type emulsion is developed by a surface developing solution. For practical purpose, the appropriate content will vary over a wide range depending upon the characteristics of silver halide emulsion, chemical structure of fogging agent and developing conditions. Nevertheless, a range of from about 0.1 mg to 1,000 mg per mol of silver of the internal latent image type silver halide emulsion is practically effective, preferably about 0.5 mg to about 700 mg per mol of silver. Where the fogging agent is incorporated into the hydrophilic colloid layer contiguous to the emulsion layer, it is adequate to incorporate the fogging agent in an amount the same as above based on the amount of silver contained in the same area of the associated internal latent image type emulsion layer. Where the fogging agent is incorporated into a processing solution, it is adequate to incorporate the fogging agent in an amount of about 0.01 to about 1 g per l of the solution.

Internal latent image type silver halide emulsions are already shown by Davey et al (U.S. Pat. No. 2,592,250) and in U.S. Pat. Nos. 3,761,276, 3,206,313, 3,317,322, 3,761,266, 3,850,637, 3,923,513, 3,736,140, 3,761,267 and 3,854,949. The internal latent image type silver halide emulsion can be clearly distinguished by the fact that the maximum density achieved in the case of developing it with "internal type" developing solution is greater than the maximum density achieved in the case of developing it with "surface type" developing solution. The internal latent image type emulsion which is suitable for the present invention has a maximum density (measured by an ordinary photographic density measurement methods) when coated onto a transparent support and exposed to light a fixed time period of between 0.01 to 1 second and then developed with Developing Solution A indicated below (an internal type developing solution) at 20° C. for 3 minutes, greater by at least 5 times than the maximum density obtained in the case of developing the silver halide exposed as described above with Developing Solution B indicated below (a surface type developing solution) at 20° C. for 4 minutes.

| Developing Solution A: | |
| --- | --- |
| Hydroquinone | 15 g |
| Monomethyl-p-aminophenol Sesquisulfate | 15 g |
| Sodium Sulfite | 50 g |
| Potassium Bromide | 10 g |
| Sodium Hydroxide | 25 g |
| Sodium Thiosulfate | 20 g |
| Water to make | 1 l |

| Developing Solution B: | |
| --- | --- |
| p-Oxyphenylglycine | 10 g |
| Sodium Carbonate | 100 g |
| Water to make | 1 l |

As internal latent image type emulsions which are suitable for the objects of the present invention, there can be employed the emulsions described in British Pat. No. 1,027,146, U.S. Pat. Nos. 3,206,313, 3,511,662, 3,447,927, 3,737,313, 3,761,276, 3,271,157, etc., in addition to the emulsion as described in U.S. Pat. No. 2,592,250 referred to above. However, the emulsions of the present invention are not limited to these.

Suitable total amount of coated silver in the silver halide photographic light-sensitive material of this invention is about 100 to about 1,500 μg/cm², preferably 300 to 700 μg/cm².

Incidentally, there is a method for producing a direct positive image which comprises exposing and then developing an internal latent image type silver halide photographic emulsion layer which is previously (i.e., prior to exposure to light) uniformly fogged. While such a previously fogged photographic emulsion can be also applicable to the present invention, a photographic emulsion of the type which is not previously fogged prior to exposure (i.e., one which is fogged during development or prior to development but after exposure) is preferred.

In the direct positive photographic light-sensitive material of the present invention, a variety of hydrophilic colloids can be employed as a binder.

As colloids employed for this purpose, there can be listed hydrophilic colloids conventionally employed in the photographic field, such as gelatin, colloidal albumin, polysaccharides, cellulose derivatives, synthetic resins, polyvinyl compounds including, e.g., polyvinyl alcohol derivatives, acrylamide polymers, etc. Hydrophobic colloids, e.g., dispersed polymerized vinyl compounds, particularly those that increase dimensional stability of photographic materials, can also be incorporated together with the hydrophilic colloid. Suitable examples of this type of compounds include water-insoluble polymers prepared by polymerizing vinyl monomers such as alkyl acrylates, alkyl methacrylates, acrylic acid, sulfoalkyl acrylates, sulfoalkyl methacrylates, etc.

A variety of photographic supports can be employed in the light-sensitive material of the present invention. The silver halide emulsion can be coated onto one side or both sides of the support.

In the light-sensitive material of the present invention, the photographic silver halide emulsion layers and other hydrophilic colloid layers can be hardened with an appropriate hardening agent. Examples of these hardening agents include aldehyde type hardening agents such as formaldehyde or mucohalogenic acids, hardening agents having active halogen, dioxane derivatives, oxypolysaccharides such as oxy starch, etc.

The photographic silver halide emulsion layer can contain other additives, particularly those useful for photographic emulsion, e.g., lubricants, stabilizers, sensitizers, light absorbing dyes, plasticizers, etc.

In addition, in the present invention, compounds which release iodine ions can be incorporated into the silver halide emulsion, and furthermore, the desired image can be obtained using a developing solution containing iodine ions.

The light-sensitive material of the present invention can contain surface active agents for a variety of purposes. Depending upon purpose, any one of nonionic, ionic and amphoteric surface active agents can be employed, which are exemplified by, e.g., polyoxyalkylene derivatives, amphoteric amino acids (including sulfobetaines), etc. Examples of such surface active agents are described in U.S. Pat. Nos. 2,600,831, 2,271,622, 2,271,623, 2,275,727, 2,787,604, 2,816,920 and 2,739,891, Belgian Pat. No. 652,862, etc.

In the light-sensitive material of the present invention, the photographic emulsion can be spectrally sensitized with sensitizing dyes to blue light, green light, red light or infrared light of relatively long wavelengths. As sensitizing dyes, there can be employed, cyanine dyes, merocyanine dyes, complex cyanine dyes, complex merocyanine dyes, holopolar cyanine dyes, styryl dyes, hemicyanine dyes, oxonol dyes, hemioxonol dyes, etc.

Useful sensitizing dyes which can be employed in accordance with the present invention are described in, for example, U.S. Pat. Nos. 3,522,052, 3,619,197, 3,713,828, 3,615,643, 3,615,632, 3,617,293, 3,628,964, 3,703,377, 3,666,480, 3,667,960, 3,679,428, 3,672,897, 3,769,026, 3,556,800, 3,615,613, 3,615,638, 3,615,635, 3,705,809, 3,632,349, 3,677,765, 3,770,449, 3,770,440, 3,769,025, 3,745,014, 3,713,828, 3,567,458, 3,625,698, 2,526,632 and 2,503,776, Japanese patent application (OPI) No. 76525/1973, Belgian Pat. No. 691,807, etc.

The sensitizing dyes employed in the present invention are used in a concentration almost equivalent to that used in ordinary negative silver halide emulsion. In particular, it is advantageous that the sensitizing dyes be employed in a dye concentration to a degree that does not substantially cause desensitization in the region of intrinsic density of silver halide emulsion. It is preferred that the sensitizing dyes be employed in a concentration of about $1.0 \times 10^{-5}$ to about $5 \times 10^{-4}$ mol per mol of silver halide, particularly in a concentration of about $4 \times 10^{-5}$ to $2 \times 10^{-4}$ mol per mol of silver halide.

Dye image-forming couplers can be incorporated into the light-sensitive material of the present invention. Alternatively, the light-sensitive material can also be developed with a developing solution containing a dye image-forming coupler. In order to incorporate a color forming agent into the silver halide emulsion of the present invention, known methods can optionally be employed. For example, methods as described in U.S. Pat. Nos. 1,055,155, 1,102,028, 2,186,849, 2,322,027 and 2,801,171 can be employed. In the present invention, developing agents, e.g., polyhydroxybenzenes, aminophenols, 3-pyrazolidones, etc., can also be incorporated in emulsion or light-sensitive material. In the present invention, the photographic emulsion can be unhardened, or can also contain tanning developing agents such as hydroquinone, catechol, etc.

The photographic emulsion of the present invention can also be utilized for obtaining desired transfer images on an image-receiving layer after appropriate development processing, in combination with a dye image-providing material for diffusion transfer capable of releasing diffusible dyes in response to development of silver halide. A dye image-releasing material which can be used in the present invention is represented by the following formula:

wherein D is a dye or dye precursor moiety which may contain a connecting group; and Y represents a moiety which releases the dye or dye precursor as a result of development processing under alkaline conditions. An example of the dye precursor includes a leuco compound.

As the dye image-providing materials, there are illustrated non-diffusible image-providing materials (dye-releasing redox compounds, hereafter referred to as "DDR compounds") which provide a diffusible dye as a result of self splitting due to oxidation by the development processing. Examples of Y effective for this type compounds are N-substituted sulfamoyl groups. For example, there can be illustrated as Y the group represented by the following formula (A):

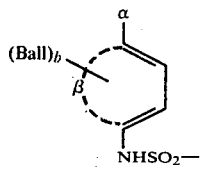
(A)

In the above formula, β represents non-metallic atoms necessary for completing a benzene ring, to which a carbon ring or a hetero ring may be fused to form, for example, a naphthalene ring, a quinoline ring, a 5,6,7,8-tetrahydronaphthalene ring, a chroman ring, etc. Further, said benzene ring or said ring wherein a carbon ring or hetero ring is fused to the benzene ring may have a substituent or substituents such as a halogen atom, an alkyl group, an alkoxy group, an aryl group, an aryloxy group, a nitro group, an amino group, an alkylamino group, an arylamino group, an amido group, a cyano group, an alkylmercapto group, a keto group, a carboalkoxy group, a hetero ring group, etc.

α represents a group of $-OG^1$ or $-NHG^2$, wherein $G^1$ represents a hydrogen atom or a group capable of forming a hydroxyl group by hydrolysis, and preferably represents a hydrogen atom,

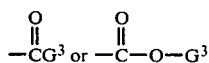

wherein $G^3$ represents an alkyl group, in particular alkyl group having 1 to 18 carbon atoms (such as a methyl group, an ethyl group, a propyl group, etc.), a halogen-substituted alkyl group having 1 to 18 carbon atoms (such as a chloromethyl group, a trifluoromethyl group, etc.), a phenyl group or a substituted phenyl group, and $G^2$ represents a hydrogen atom, an alkyl group having 1 to 22 carbon atoms or a hydrolyzable group. Preferable examples of said hydrolyzable group represented by $G^2$ are

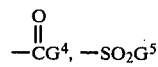

or $-SOG^5$, wherein $G^4$ represents an alkyl group having 1 to 4 carbon atoms (such as a methyl group); a halogen-substituted alkyl group (such as mono-, di- or trichloromethyl group or a trifluoromethyl group); an alkylcarbonyl group (such as an acetyl group); an alkoxy group; a substituted phenyl group (such as a nitrophenyl group or a cyanophenyl group); a phenyloxy group unsubstituted or substituted by a lower alkyl group or a halogen atom; a carboxyl group; an alkyloxycarbonyl group; an aryloxycarbonyl group; an alkylsulfonylethoxy group; or an arylsulfonylethoxy group; and $G^5$ represents a substituted or unsubstituted alkyl or aryl group.

Further, b is an integer of 0, 1 or 2, and b represents 1 or 2, preferably 1, except when said α represents $-NHG^2$ wherein $G^2$ represents an alkyl group making the compound of the general formula (A) immobile and non-diffusible, namely, when α represents a group represented by $-OG^1$ or $-NHG^2$ wherein $G^2$ represents a hydrogen atom, an alkyl group having 1 to 8 carbon atoms or a hydrolyzable group. Ball represents a ballast group which renders the dye image-releasing group nondiffusible. Examples of the ballast group are well known to one skilled in the art of color diffusion transfer photography.

Specific examples of this type Y and the ballast group are described in U.S.B. No. 351,673, U.S. Pat. No. 3,928,312 and Japanese patent application (OPI) No. 50736/1978.

As the other examples of Y suitable for this type of compounds, there are illustrated the group represented by the following formula (B):

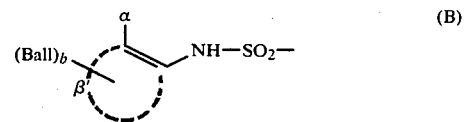
(B)

In the above formula, Ball, α and b are the same as defined in the formula (A), β' represents atoms necessary for forming a carbon ring, for example, a benzene ring, to which a carbon ring or a hetero ring may further be fused to form a naphthalene ring, a quinoline ring, a 5,6,7,8-tetrahydronaphthalene ring, a chroman ring, etc. The above-described various rings may be further substituted by a halogen atom, an alkyl group, an alkoxy group, an aryl group, an aryloxy group, a nitro group, an amino group, an alkylamino group, an arylamino group, an amido group, a cyano group, an alkylmercapto group, a keto group, a carboalkoxy group, a hetero ring or the like. Specific examples of this type Y are described in U.S. Pat. Nos. 4,055,428 and 4,053,312.

As the further examples of Y suitable for this type compounds, there are illustrated the group represented by the general formula (C):

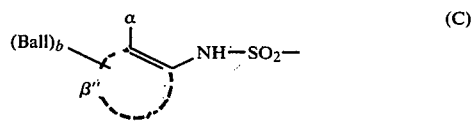
(C)

In the above formula, Ball, α and b are the same as defined in the formula (A), and β'' represents atoms necessary for forming a hetero ring such as a pyrazole ring, a pyridine ring, etc., to which a carbon ring or a hetero ring may further be fused. The above-described rings may be substituted by the same substituents as those for the rings described in the formula (B). Specific examples of this type Y are described in Japanese Patent Application (OPI) No. 104343/1976.

As the still further examples of Y suitable for this type compounds, there are illustrated those represented by the general formula (D):

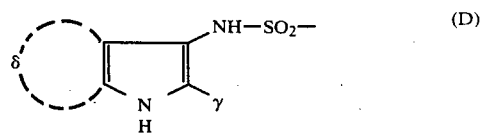
(D)

In the above formula, γ preferably represents a hydrogen atom; an alkyl group, aryl group or hetero ring group which may be unsubstituted or substituted; or $-CO-G^6$ wherein $G^6$ represents $-OG^7$, $-S-G^7$ or

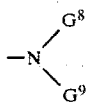

(herein $G^7$ represents a hydrogen atom, an alkyl group, a cycloalkyl group or an aryl group, which may be substituted, $G^8$ represents the same group as $G^7$ or an acyl group derived from an aliphatic or aromatic carboxylic acid or from sulfonic acid, and $G^9$ represents a hydrogen atom or a substituted or unsubstituted alkyl group), δ represents a necessary residue for completing a fused benzene ring which ring may have one or more substituents, and γ and/or the substituents on said fused benzene ring completed by δ is a ballast group or a ballast-containing group. Specific examples of this type Y are described in Japanese patent application (OPI) Nos. 104343/76 and 46730/78.

As the still further examples of Y suitable for this type compounds, there are illustrated the group represented by the general formula (E):

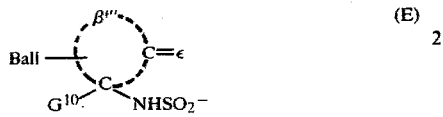

In the above formula, Ball is the same as defined in the formula (A), ε represents an oxygen atom or =NG″, (G″ represents a hydroxyl group or an amino group which may have a substituent) and, when ε represents =NG″, a typical example of G″ is that in =C=N—G″ formed by the dehydration reaction between a carbonyl reagent of $H_2N$—G″ and a ketone group. Examples of the compound of $H_2N$—G″ are hydroxylamines, hydrazines, semicarbazides, thiosemicarbazides, etc. To be specific, there are illustrated, as the hydrazines, hydrazine, phenylhydrazine, substituted phenylhydrazine having in the phenyl moiety a substituent or substituents such as an alkyl group, an alkoxy group, a carboalkoxy group, a halogen atom, etc., isonicotinic acid hydrazine, etc. As the semicarbazides, there are illustrated, phenylsemicarbazide or substituted phenylsemicarbazide substituted by an alkyl group, an alkoxy group, a carboalkoxy group, a halogen atom, etc. As the semithiocarbazides, there are illustrated the same derivatives as with semicarbazides.

β‴ in the formula represents a 5-, 6- or 6-membered saturated or unsaturated non-aromatic hydrocarbons. To be specific, there are illustrated, for example, cyclopentanone, cyclohexanone, cyclohexenone, cyclopentenone, cycloheptanone, cycloheptenone, etc.

These 5- to 7-membered non-aromatic hydrocarbon rings may be fused to other ring at a suitable position to form a fused ring system. As the other ring, various rings may be used regardless of whether they show aromaticity or not or whether they are hydrocarbon rings or hetero rings. However, in the case of a fused ring being formed, fused systems wherein benzene and the above-described 5- to 7-membered non-aromatic hydrocarbon ring are fused to each other such as indanone, benzcyclohexenone, benzcycloheptenone, etc., are preferable in the present invention.

The above-described 5- to 7-membered non-aromatic hydrocarbon rings or the above-described fused rings may have one or more substituents such as an alkyl group, an aryl group, an alkyloxy group, an aryloxy group, an alkylcarbonyl group, an arylcarbonyl group, an alkylsulfonyl group, an arylsulfonyl group, a halogen atom, a nitro group, an amino group, an alkylamino group, an arylamino group, an amido group, an alkylamido group, an arylamido group, a cyano group, an alkylmercapto group, an alkyloxycarbonyl group, etc.

$G^{10}$ represents a hydrogen atom, or a halogen atom such as fluorine, chlorine or bromine.

Specific examples of this type Y are described in Japanese Patent Application (OPI) No. 3819/1978.

As the still further examples of Y for the compounds of the present invention, there are those described in, for example, U.S. Pat. Nos. 3,443,930, 3,443,939, 3,628,952, 3,844,785, 3,443,943, 3,227,551, 3,227,554, 3,443,940, 3,658,524, 3,698,897, 3,725,062, 3,728,113, 3,751,406, 3,929,760, 3,931,144, 3,932,381, 4,013,633, 3,932,380, 3,954,476, 3,942,987, 4,013,635, British Pat. Nos. 840,731, 904,364 and 1,038,331, German patent application (OLS) Nos. 1,930,215, 2,214,381, 2,228,361, 2,317,134 and 2,402,900, French Pat. No. 2,284,140, Japanese patent application Nos. 64533/1977 and 58318/1977.

As the different type compounds of the dye image-providing compounds, there are illustrated non-diffusible compounds (dye-releasing couplers) which release a diffusible dye upon coupling reaction with an oxidation product of a color developing agent oxidized by silver halide. As the examples of Y effective for such compounds, the groups described in U.S. Pat. No. 3,227,550 are typical. For example, there are illustrated as Y those represented by the following general formula (F):

(Ball-Coup)$_t$—Link— (F)

wherein Coup represents a coupler residue capable of coupling with an oxidation product of a color developing agent, for example, a 5-pyrazolone type coupler residue, a phenol type coupler residue, a naphthol type coupler residue, an indanone type coupler residue or an open chain ketomethylene coupler residue, Ball represents a ballast group. Link represents a group bonded to an active cite of Coup moiety, which bond with Coup moiety will be split upon coupling reaction between the dye image-providing material containing the group represented by the formula (F) as Y and an oxidation product of a color developing agent. Examples of the Link are an azo group, an azoxy group, —O—, —Hg—, an alkylidene group, —S—, —S—S— or —NHSO$_2$—, and t represents 1 or 2 when Link represents an alkylidene group or represents 1 when Link represents other group described above.

Of groups Y represented by the formula (F), preferable groups are those wherein Coup represents a phenol type coupler residue, a naphthol type coupler residue or an indanone type coupler residue, and Link represents —NHSO$_2$—.

Of the above-described compounds, particularly preferable ones are dye-releasing redox compounds and effective Y groups are N-substituted sulfamoyl groups. As the N-substituents for the N-substituted sulfamoyl groups, carbon ring groups (in particular, o- or p-hydroxyaryl group having a ballast group bonded thereto being preferable) or hereto ring groups are desirable. As the examples of N-carbon ring substituted sulfamoyl groups, those represented by the formulae (A) and (B) are preferable. As the examples of N-hetero ring substituted sulfamoyl groups, those represented by the formulae (C) and (D) are preferable. As Y, the group represented by the general formula (B) are particularly preferable.

If the fogging agent is employed in combination with such DRR compounds, the temperature dependency upon processing is markedly reduced.

The DRR compound which can be used in the present invention in conventional amounts. The DRR compound can be in the silver halide emulsion layer or an adjacent hydrophilic colloid layer.

Specific examples of DRR compounds include, in addition to those as described in the above-described patent publications, 1-hydroxy-2-tetramethylenesulfamoyl-4-[3'-methyl-4'-(2''-hydroxy-4''-methyl-5''-hexadecyloxyphenylsulfamoyl)-phenylazo]naphthalene as a magenta dye-forming substance, 1-phenyl-3cyano-4-{3'-[2''-hydroxy-4''-methyl-5''-(2''',4'''-di-t-pentyl-phenoxyacetamino)phenylsulfamoyl]phenylazo}-5-pyrazolone as a yellow dye image-forming substance, etc.

For developing the light-sensitive material of the present invention, a variety of known developing agents can be employed. That is, polyhydroxybenzenes, e.g., hydroquinone, 2-chlorohydroquinone, 2-methylhydroquinone, catechol, pyrogallol, etc.; aminophenols, e.g., p-aminophenol, N-methyl-p-aminophenol, 2,4-diaminophenol, etc.; 3-pyrazolidones, e.g., 1-phenyl-3-pyrazolidones, 4,4-dimethyl-1-phenyl-3-pyrazolidone, 5,5-dimethyl-1-phenyl-3-pyrazolidone, etc.; ascorbic acids, and the like can be employed singly or as combination thereof. In addition, to obtain dye images in the presence of dye-forming couplers, aromatic primary amine developing agents, preferably p-phenylenediamine type developing agents can be used. Specific examples thereof include 4-amino-3-methyl-N,N-diethylaniline hydrochloride, N,N-diethyl-p-phenylenediamine, 3-methyl-4-amino-N-ethyl-N-$\beta$-(methanesulfonamido)-ethylaniline, 3-methyl-4-amino-N-ethyl-N-($\beta$-sulfoethyl)-aniline, 3-ethoxy-4-amino-N-ethyl-N-($\beta$-sulfoethyl)aniline, 4-amino-N-ethyl-N-($\beta$-hydroxyethyl)aniline. Such developing agents can be incorporated into alkaline processing compositions (processing element) or can also be incorporated into appropriate layers of the light-sensitive element.

In the case of using DRR compound in the present invention, any silver halide developing agent can be employed as long as the agent is able to cross-oxidize the DRR compounds.

The developing agent can contain, as a preservative, sodium sulfite, potassium sulfite, ascorbic acid, reductones (e.g., piperidinohexose reductone), etc.

The light-sensitive material of the present invention can provide direct positive images by developing the material using a surface developing solution. The surface developing solution induces the development process substantially with latent images or fogging nuclei present on the surface of silver halide grains. Though it is preferred not to contain any silver halide dissolving agent in the developing solution, a small amount of the silver halide dissolving agent (e.g., sulfites) can be contained in the developing solution as long as internal latent images do not substantially contribute to development until the development due to the surface development center of silver halide grains is completed.

The developing solution can contain, as an alkali agent and a buffering agent, sodium hydroxide, potassium hydroxide, sodium carbonate, potassium carbonate, trisodium phosphate, sodium metaborate, etc. The amount of these agents is selected so as to render the pH of the developing solution to 10 to 13, preferably pH to 11 to 12.5.

The developing solution can also contain color development accelerators such as benzyl alcohol, or the like. Further, it is advantageous that the developing solution contains, in order to lessen the reduction in the minimum density of direct positive images, compounds which are usually employed as anti-fogging agents, for example, benzimidazoles, e.g., 5-nitrobenzimidazole; benzotriazoles, e.g., benzotriazole, 5-methylbenzotriazole, etc.

The light-sensitive material of the present invention can also be processed with a viscous developing solution.

The viscous developing solution is a liquid state composition in which processing components necessary for development of silver halide emulsion and for formation of diffusion transfer dye images are contained; a major component of the solvent is water and in addition thereto, hydrophilic solvents such as methanol, methyl Cellosolve, etc., are contained therein some case. The processing composition contains an alkali in an amount sufficient to maintain pH necessary for developing the emulsion layer(s) and to neutralize acids (e.g., hydrohalic acids such as hydrobromic acid, carboxylic acids such as acetic acid, etc.) formed during various processings for development and formation of dye images. As alkalis, there may be employed alkali metal- or alkaline earth metal salts, or amines such as lithium hydroxide, sodium hydroxide, potassium hydroxide, calcium hydroxide dispersion, hydroxylated tetramethyl ammonium, sodium carbonate, trisodium phosphate, diethylamine, etc. It is desired that alkali hydroxides be incorporated in the developing solution in such an amount as having pH of preferably about 12 or more at room temperature, more preferably pH of 14 or more for color diffusion transfer photography. More preferably, the processing composition contains hydrophilic polymers of high molecular weight, such as polyvinyl alcohol, hydroxyethyl cellulose, sodium carboxymethyl cellulose. It is desired that these polymers be employed so as to impart viscosity above 1 poise at room temperature preferably several hyndreds (500 to 600) to 1,000 poise, to the processing composition.

Further, it is advantageous particularly in the case of a mono sheet film unit that the processing composition contain light absorbing agents such as $TiO_2$, carbon black, pH-indicating dyes for preventing the silver halide emulsion from fogging due to outside light during or after processing, or desensitizers as described in U.S. Pat. No. 3,579,333. In addition, developing inhibitors such as benzotriazole can be incorporated into the processing composition.

It is preferred that the above-described viscous processing composition be employed in a rupturable container as described in U.S. Pat. Nos. 2,543,181, 2,643,886, 2,653,732, 2,723,051, 3,056,491, 3,152,515, etc.

Where the light-sensitive material of the present invention is employed for diffusion transfer photography, it is preferred that the light-sensitive material be in the form of a film unit. A photographic film unit, that is, a film unit designed so as to enable processing by passing the film unit between a pair of side-by-side disposed pressing materials basically comprises the three elements below:

(1) a light-sensitive element containing the fogging agent of the present invention, (2) an image receiving element, and (3) the processing element; e.g., which contains a means for releasing the alkaline processing composition and contains the silver halide developing agent.

A preferred embodiment of this photographic film unit is a type unified by laminating and the type disclosed in Belgian Pat. No. 757,959. According to this embodiment, the film unit comprises a transparent support having coated thereon, in succession, an image receiving layer, a substantially opaque light reflective layer (e.g., a $TiO_2$ layer or a carbon black layer), and a light-sensitive element comprising single or plural silver halide light-sensitive layers in combination with DRR compounds, and further thereon laminated a transparent cover sheet. A rupturable container containing an alkaline processing composition comprising an opacifying agent (e.g., carbon black) is disposed adjacent to the outermost layer of the above-described light-sensitive layers and the transparent cover sheet. Such a film unit is exposed to light through the transparent cover sheet; upon taking the unit out of a camera, the container is ruptured by the pressing materials to thereby develop the processing composition (containing the opacifying agent) is spread over the entire surface between a protective layer on the light-sensitive layers and the cover sheet. By doing this, the film unit is shielded from light as development proceeds. It is preferred that a neutralizing layer and further, if necessary, a neutralizing rate controlling layer (timing layer) be coated, in succession, onto a support of the cover sheet.

In addition, other useful embodiments utilizing laminate layers in which DRR compounds or diffusible dye releasing couplers are employed are described in U.S. Pat. Nos. 3,415,644, 3,415,645, 3,415,646, 3,647,487 and 3,635,707, German Patent Application (OLS) No. 2,426,980, etc.

The present invention will be further explained by reference to the examples below. However, the present invention is not limited thereto. Unless otherwise indicated, all parts, percents, ratios, etc., are by weight.

EXAMPLE 1

Onto a polyethylene terephthalate transparent support were coated in succession the following layers below to prepare four kinds of light-sensitive sheets (A) to (D).

(1) mordant layer containing the polymer (3.0 g/m$^2$) described in U.S. Pat. No. 3,898,088 and having the repeating unit indicated below:

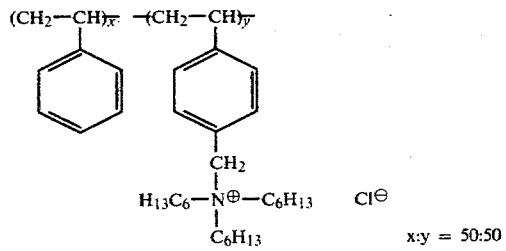

x:y = 50:50 and gelatin (3.0 g/m$^2$)

(2) white reflective layer containing 20 g/m$^2$ of titanium oxide and 2.0 g/m$^2$ of gelatin (3) light-shielding layer containing 2.70 g/m$^2$ of carbon black and 2.70 g/m$^2$ of gelatin (4) layer containing the magenta DRR compound (0.45 g/m$^2$) indicated below, diethyllaurylamide (0.10 g/m$^2$), 2,5-di-t-butylhydroquinone (0.0074 g/m$^2$) and gelatin (0.76 g/m$^2$)

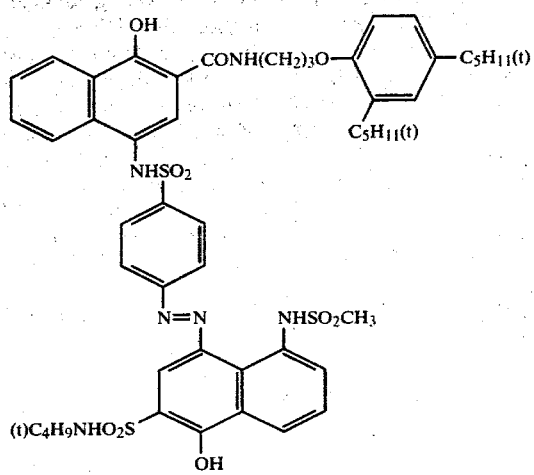

(5) layer containing green sensitive internal latent image type direct positive silver bromide emulsion (internal latent image type emulsion prepared in the same manner as described in Example 7, Emulsion B of U.S. Pat. No. 3,761,276; 1.4 g/m$^2$ calculated as the amount of silver, 1.0 g/m$^2$ of gelatin), sodium 5-pentadecylhydroquinone-2-sulfonate (0.11 g/m$^2$), and a fogging agent in an amount indicated below:

| | | |
|---|---|---|
| Light-sensitive sheet (A) | none | — |
| Light-sensitive sheet (B) | Compound 1 | 11.5 mg/mol of Ag |
| Light-sensitive sheet (C) | Compound 2 | 12.3 mg/mol of Ag |
| Light-sensitive sheet (D) | Compound 5 | 14.8 mg/mol of Ag |

(6) layer of gelatin (0.94 g/m$^2$)

The above-described light-sensitive sheets (A) to (D) were processed in combination with each element shown below.

| Processing Solution: | | |
|---|---|---|
| 1-Phenyl-4-methyl-4-hydroxymethyl-3-pyrazolidone | 10 | g |
| Methylhydroquinone | 0.18 | g |
| 5-Methylbenzotriazole | 4.0 | g |
| Sodium Sulfite (anhydrous) | 1.0 | g |
| Carboxymethyl Cellulose Na Salt | 40.0 | g |
| Carbon Black | 150 | g |
| Potassium Hydroxide (28% aq. soln.) | 200 | cc |
| H$_2$O | 550 | cc |

0.8 g of the processing solution of the above composition was filled into each pressure rupturable container Cover Sheet:

Onto a polyethylene terephthalate support were coated an acid polymer layer (neutralizing layer) containing 15 g/m$^2$ of polyacrylic acid (a 10 wt% aqueous solution having viscosity of about 1,000 cp), a neutralization timing layer containing 3.8 g/m$^2$ of acetyl cellulose (hydrolysis of 100 g of the acetyl cellulose forms 39.4 g of acetyl groups), and 0.2 g/m$^2$ of a styrene-maleic anhydride copolymer (composition (molar) ratio: styrene:maleic anhydride is about 60:40, molecular weight: about 50,000) thereon, to thereby prepare a cover sheet.

Processing Step:

The above-described cover sheet was laminated on the above-described light-sensitive sheet. Exposure was performed through a color test chart from the cover sheet side. Thereafter, the processing solution described above was spread between both sheets in a thickness of 75 microns (with assistance of a roller). The processing was carried out at 25° C. After processing, the green density of the images formed on the image-receiving layer was measured 1 hour after the processing through the transparent support of the lightsensitive sheet using a Macbeth reflection densitometer. The results thereof are shown in Table 1.

It is apparent from the results shown in Table 1 that the compounds of the present invention act as excellent fogging agents.

TABLE 1

| Light-Sensitive Element | $D_{max}$ | $D_{min}$ |
| --- | --- | --- |
| A | 0.27 | 0.25 |
| B | 2.05 | 0.26 |
| C | 1.88 | 0.31 |
| D | 1.92 | 0.29 |

EXAMPLE 2

Onto a polyethylene terephthalate transparent support, the following layers were coated in succession to prepare a light-sensitive sheet (E).

(1) mordant layer same as in Example 1
(2) white reflective layer same as in Example 1
(3) light-shielding layer same as in Example 1
(4) layer containing a cyan DRR compound (0.5 g/m²) indicated below, diethyllauryl amide (0.25 g/m²) and gelatin (1.14 g/m²)

(5) layer containing red sensitive internal latent image type direct positive silver bromide emulsion (internal latent image type emulsion prepared in accordance with the method described in Example 7, Emulsion B of U.S. Pat. No. 3,761,276; 1.9 g/m² calculated as the amount of silver, 1.4 g/m² of gelatin), fogging agent A in the amount indicated in Table 2 below, and sodium 5-pentadecyl-hydroquinone-2-sulfonate (0.13 g/m²)

(6) layer containing gelatin (2.6 g/m²) and 2,5-dioctylhydroquinone (1.0 g/m²)

(7) a layer the same as layer (4) of Example 1 except containing the magenta DRR compound indicated below

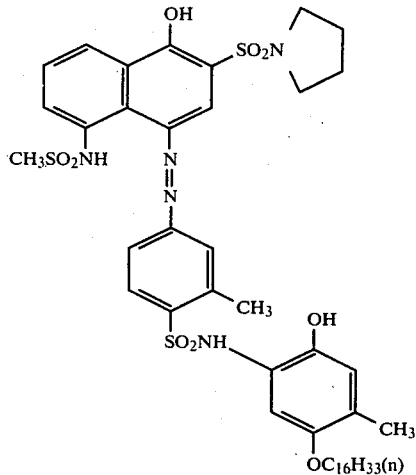

(8) a green sensitive internal latent image type direct positive emulsion layer as in Example 1 except containing Fogging Agent A in the amount indicated in Table 2 below.

(9) a layer same as layer (6) described above

(10) a layer containing the yellow DRR compound (0.78 g/m²) indicated below, diethyllauryl amide (0.16 g/m²), 2.5-di-t-butylhydroquinone (0.012 g/m²) and gelatin (0.78 g/m²)

(11) layer containing blue sensitive internal latent image type direct positive silver bromide emulsion (internal latent image type emulsion prepared in accordance with the method described in Example 7, Emulsion B of U.S. Pat. No. 3,761,276; 2.2 g/m² calculated as the amount of silver, 1.7 g/m² of gelatin), Fogging Agent A (in an amount indicated in Table 2 below) and sodium 5-pentadecyl-hydroquinone-2-sulfonate (0.094 g/m²)

(12) layer containing gelatin (0.94 g/m²)

Further, light-sensitive sheets (F) and (G) were prepared in a manner similar to light-sensitive sheet (E) except that Fogging Agent B and fogging agent (Compound 1) of the present invention were employed instead of Fogging Agent A in the layers (5), (8) and (10) described above.

TABLE 2

| Light Sensitive Element | Fogging Agent | Amount Added (mg/1 mol Ag) | | |
|---|---|---|---|---|
| | | Blue Sensitive Layer | Green Sensitive Layer | Red Sensitive Layer |
| E | Fogging Agent A | 1,700 | 1,500 | 2,000 |
| F | Fogging Agent B | 10 | 9.5 | 12 |
| G | Compound 1 | 14 | 15 | 18 |

Fogging Agent A (for comparison)

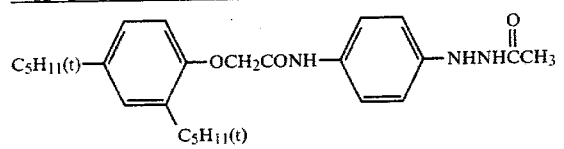

Fogging Agent B (for comparison)

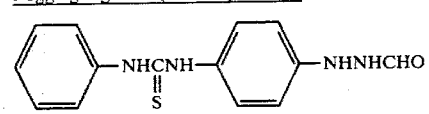

Compound 1 (this invention)

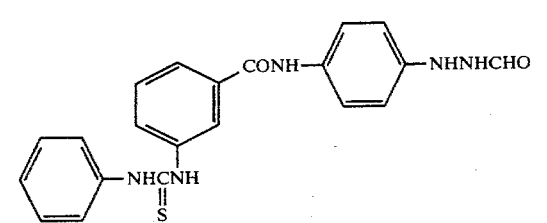

Processing Solution

The same processing solution used in Example 1.

Cover Sheet

Onto a polyethylene terephthalate support, the following coatings were applied in succession.

(1) In 1 kg of a 20% solution of an acrylic acidbutyl acrylate (8:2 in a molar ratio) copolymer having average molecular weight of 50,000 (solvent: acetone-water=3:1 (in a volume ratio)) was dissolved 3.8 g of 5-(2-cyanoethylthio)-1-phenyltetrazole. The solution was coated in an amount of 110 g per 1 m² to obtain a layer having a thickness of about 20 microns.

(2) In an acetone-cyclohexane (3:1 in a volume ratio) solvent mixture were dissolved 55 g of cellulose acetate having acetylation degree of 52.1% (the weight of acetic acid released by hydrolysis was 0.521 g per 1 g of the sample), and 5 g of a styrene-maleic anhydride (1:1 in a molar ratio) copolymer having average molecular weight of 10,000. The solution so obtained was coated in an amount of 50 g per 1 m² to obtain a layer having a thickness of about 2.6 microns.

(3) Using a solution (10% solution as solid component) of a polymer latex obtained by emulsion-polymerizing styrene-butyl acrylate-acrylic acid in a weight ratio of 52:42:6, coating was made in an amount of 30 cc per 1 m².

Processing Step

The above-described cover sheet was laminated on the above-described light-sensitive sheet. Imagewise exposure was performed through a continuous gradation wedge from the cover sheet side. Thereafter, the above-described processing solution was spread in a thickness of 80 microns with the assistance of a pressure roller. The processing was performed at 15° C., 25° C. and 35° C., respectively. After processing, the photographic properties of the color positive images obtained with the respective sheets are shown in Table 3.

TABLE 3

| Light-Sensitive Sheet | | Photographic Property | | | | | | | | |
|---|---|---|---|---|---|---|---|---|---|---|
| | | $D_{max}$ | | | $D_{min}$ | | | $S_{rel}$[1] | | |
| | | 15° C. | 25° C. | 35° C. | 15° C. | 25° C. | 35° C. | 15° C. | 25° C. | 35° C. |
| E | B[2] | 1.35 | 1.76 | 1.92 | 0.22 | 0.23 | 0.28 | 125 | 100 | 86 |
| | G | 1.46 | 1.85 | 1.98 | 0.23 | 0.23 | 0.27 | 121 | 100 | 82 |
| | R | 1.57 | 1.95 | 2.01 | 0.30 | 0.31 | 0.37 | 133 | 100 | 79 |
| F | B | 1.74 | 1.66 | 1.62 | 0.23 | 0.23 | 0.26 | 95 | 100 | 109 |
| | G | 1.84 | 1.70 | 1.73 | 0.26 | 0.24 | 0.26 | 70 | 100 | 112 |
| | R | 1.92 | 1.93 | 1.82 | 0.31 | 0.30 | 0.32 | 59 | 100 | 133 |
| G | B | 1.58 | 1.59 | 1.68 | 0.24 | 0.24 | 0.26 | 95 | 100 | 107 |
| | G | 1.68 | 1.65 | 1.70 | 0.23 | 0.24 | 0.27 | 92 | 100 | 106 |
| | R | 1.80 | 1.86 | 1.87 | 0.30 | 0.30 | 0.32 | 79 | 100 | 102 |

[1]$S_{rel}$ is a relative sensitivity and indicates a reciprocal value of the exposure amount required to obtain the ½ density of the sum of the maximum density and the minimum density, assuming that the sensitivity in each light-sensitive silver halide emulsion layer processed at 25° C. is 100.
[2]B, R and G each represents a blue sensitive layer, a green sensitive layer and a red sensitive layer.

As can clearly be seen from the results shown in the table above, Light-Sensitive Sheet G using Compound 1 in accordance with the present invention is less temperature-dependent during development in comparison to Light-Sensitive Sheets E and F using the known fogging agents. That is, when the fogging agent of the present invention was employed, the reduction in $D_{max}$ is small, as compared to when the fogging agent of Compound A type is used. In addition, variations in $D_{max}$ or Srel are markedly reduced with respect to the change in temperature during development. Furthermore, with the fogging agent of the present invention, the change in Srel in the G layer and R layer due to changes in temperature during development is markedly reduced.

While the invention has been described in detail and with reference to specific embodiments thereof, it will be apparent to one skilled in the art that various changes and modifications can be made therein without departing from the spirit and scope thereof.

What is claimed is:

1. A direct positive silver halide photographic light-sensitive material comprising a support having coated thereon an internal latent image type light-sensitive photographic emulsion layer that contains a light-sensitive silver halide of the type which is not previously fogged, and a hydrophilic colloid layer adjacent to said emulsion layer, at least one of said layers containing a compound represented by the formula (I) and present in an amount to give a suitable maximum density when said material is developed by a surface developing solution:

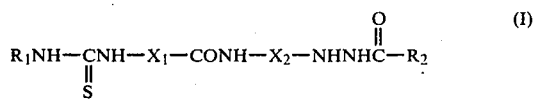

wherein $R_1$ represents a substituted or unsubstituted alkyl group, a substituted or unsubstituted alkenyl group, a substituted or unsubstituted phenyl group or a substituted or unsubstituted naphthyl group; $R_2$ represents a hydrogen atom, a substituted or unsubstituted alkyl group, a substituted or unsubstituted alkenyl group, a substituted or unsubstituted phenyl group or a substituted or unsubstituted naphthyl group; and $X_1$, and $X_2$, which are the same or different, each represents a substituted or unsubstituted phenylene group or a substituted or unsubstituted naphthylene group.

2. The direct positive silver halide photographic light-sensitive material of claim 1, wherein said light-sensitive silver halide photographic emulsion layer or adjacent hydrophilic colloid layer contains a diffusible dye releasing type dye image providing material having an o-hydroxyarylsulfamoyl group.

3. The direct positive silver halide photographic light-sensitive material of claim 1, wherein said compound of the formula (I) is present in an amount of about 0.1 mg to 1,000 mg per mol of silver halide.

4. The direct positive silver halide photographic light-sensitive material of claim 1, wherein said compound of the formula (I) is present in an amount of 0.5 mg to 700 mg per mol of silver halide.

5. The direct positive silver halide photographic light-sensitive material of claim 1, wherein said silver halide emulsion layer is sensitized to red, green or blue light.

6. The direct positive silver halide photographic light-sensitive material of claim 1, wherein said silver halide emulsion layer contains a sensitizing dye selected from the group consisting of cyanine dyes, merocyanine dyes, complex cyanine dyes, complex merocyanine dyes, holopolar cyanine dyes, styryl dyes, hemicyanine dyes, oxonol dyes and hemioxonol dyes.

7. The direct positive silver halide photographic light-sensitive material of claim 6, wherein said dye is present in an amount of $1.0 \times 10^{-5}$ to about $5 \times 10^{-4}$ mol per mol of silver halide.

8. The direct positive silver halide photographic light-sensitive material of claim 1, wherein the alkyl group for $R_1$ and $R_2$ is an unsubstituted alkyl group or an alkyl group substituted with an alkoxy group, a halogen atom, an aryl group, a hydroxy group, an alkoxycarbonyl group, an aryloxycarbonyl group, an amido group or an acyloxy group.

9. The direct positive silver halide photographic light-sensitive material of claim 1, wherein the aromatic residue for $R_1$ and $R_2$ is a phenyl group, a naphthyl group, or a phenyl or naphthyl group substituted with an alkyl group, an alkoxy group, a halogen atom, a hydroxy group, an alkoxycarbonyl group, an aryloxycarbonyl group, an amido group or an acyloxy group.

10. The direct positive silver halide photographic light-sensitive material of claim 1, wherein $X_1$ and $X_2$ are a phenylene group, a naphthylene group or a phenylene or naphthylene group substituted with an alkyl group, an alkoxy group, a halogen atom, a hydroxy group, an alkoxycarbonyl group, an aryloxycarbonyl group, an amido group or an acyloxy group.

11. The direct positive silver halide photographic light-sensitive material of claim 10, wherein $X_1$ and $X_2$ are a phenylene group.

12. The direct positive silver halide photographic light-sensitive material of claim 11, wherein the

group is connected to the

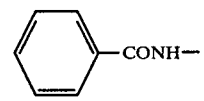

group at the meta or para position, and the

group is connected with the

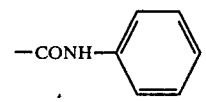

group at the meta or para position thereof.

13. The direct positive silver halide photographic light-sensitive material of claim 1, wherein the said light-sensitive silver halide photographic emulsion layer or adjacent hydrophilic colloid layer contains a diffusible dye-releasing type dye image-providing material.

14. The direct positive silver halide photographic light-sensitive material of claim 13, wherein the dye image-providing material is a diffusible dye releasing redox compound having an N-substituted sulfamoyl group as a redox center.

15. The direct positive silver halide photographic light-sensitive material of claim 14, wherein the N-substituted sulfamoyl group is an N-hydrocarbon ring or heterocyclic ring substituted sulfamoyl group.

16. A method for forming a direct-positive image which comprises image-wise exposing and subsequent developing of a light-sensitive silver halide photographic material having a support carrying thereon at least one internal latent image type light-sensitive emulsion layer which contains a light-sensitive silver halide of the type that is not previously fogged, in the presence of a compound represented by the formula (I) of claim 1.

* * * * *